(12) United States Patent
Harris

(10) Patent No.: US 7,282,337 B1
(45) Date of Patent: Oct. 16, 2007

(54) METHODS FOR INCREASING ACCURACY OF NUCLEIC ACID SEQUENCING

(75) Inventor: Timothy D. Harris, Toms River, NJ (US)

(73) Assignee: Helicos BioSciences Corporation, Cambridge, MA (US)

( * ) Notice: Subject to any disclaimer, the term of this patent is extended or adjusted under 35 U.S.C. 154(b) by 0 days.

(21) Appl. No.: 11/404,695

(22) Filed: Apr. 14, 2006

Related U.S. Application Data

(63) Continuation-in-part of application No. 11/404,675, filed on Apr. 14, 2006, now abandoned.

(51) Int. Cl.
*C12Q 1/68* (2006.01)

(52) U.S. Cl. .......................................................... 435/6
(58) Field of Classification Search ..................... None
See application file for complete search history.

(56) References Cited

U.S. PATENT DOCUMENTS 6,818,395 B1 * 11/2004 Quake et al. .................. 435/6

\* cited by examiner

*Primary Examiner*—Young J. Kim
(74) *Attorney, Agent, or Firm*—Cooley Godward Kronish LLP; Thomas C. Meyers

(57) ABSTRACT

The invention provides methods for improving the accuracy of a sequencing-by-synthesis reaction by sequencing at least a portion of a template and at least a portion of template complementary sequence.

8 Claims, 1 Drawing Sheet

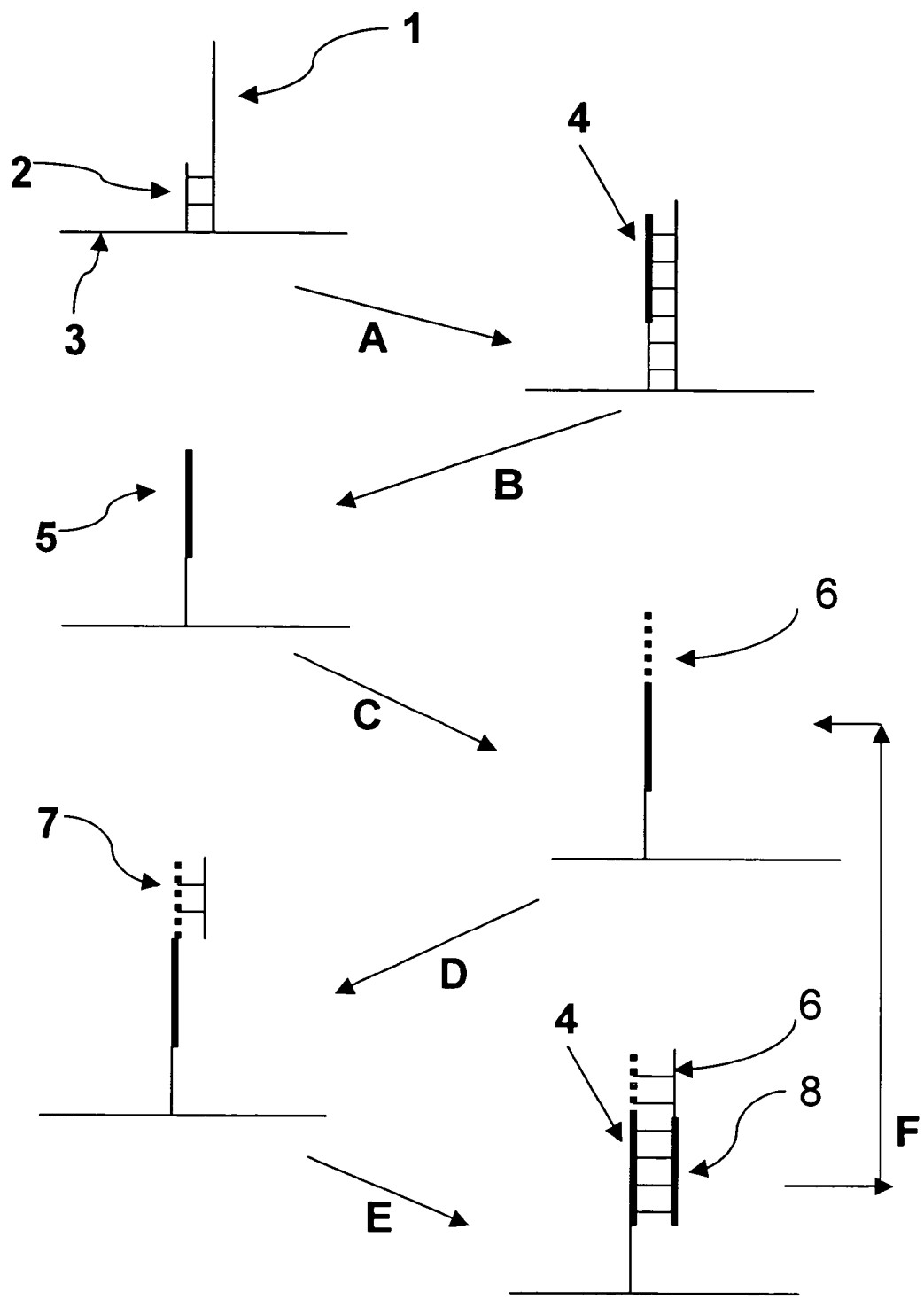
FIGURE

METHODS FOR INCREASING ACCURACY OF NUCLEIC ACID SEQUENCING

This application is a continuation-in-part of U.S. patent application Ser. No. 11/404,675, filed Apr. 14, 2006 now abandoned.

TECHNICAL FIELD OF THE INVENTION

The invention generally relates to methods for increasing accuracy in nucleic acid synthesis reactions.

BACKGROUND OF THE INVENTION

In vitro nucleic acid synthesis is a foundation of many fundamental research and diagnostic tools, such as nucleic acid amplification and sequencing. In a template-dependent nucleic acid synthesis reaction, the sequential addition of nucleotides is catalyzed by a nucleic acid polymerase. Depending on the template and the nature of the reaction, the nucleic acid polymerase may be a DNA polymerase, an RNA polymerase, or a reverse transcriptase.

The accuracy of template-dependent nucleic acid synthesis depends in part on the ability of the polymerase to discriminate between complementary and non-complementary nucleotides. Normally, the conformation of the polymerase enzyme favors incorporation of the complementary nucleotide. However, there is still an identifiable rate of misincorporation that depends upon factors such as local sequence and the base to be incorporated.

Synthetic or modified nucleotides and analogs, such as labeled nucleotides, tend to be incorporated into a primer less efficiently than naturally-occurring nucleotides. The reduced efficiency with which the unconventional nucleotides are incorporated by the polymerase can adversely affect the performance of sequencing techniques that depend upon faithful incorporation of such unconventional nucleotides.

Single molecule sequencing techniques allow the evaluation of individual nucleic acid molecules in order to identify changes and/or differences affecting genomic function. In single molecule techniques, a nucleic acid fragment is attached to a solid support such that at least a portion of the nucleic acid fragment is individually optically-resolvable. Sequencing is conducted using the fragments as templates. Sequencing events are detected and correlated to the individual strands. See Braslavsky et al., Proc. Natl. Acad. Sci., 100: 3960-64 (2003), incorporated by reference herein. Because single molecule techniques do not rely on ensemble averaging as do bulk techniques, errors due to misincorporation can have a significant deleterious effect on the sequencing results. The incorporation of a nucleotide that is incorrectly paired, under standard Watson and Crick base-pairing, with a corresponding template nucleotide during primer extension may result in sequencing errors. Furthermore, where the template being sequenced is present in only one or a few copies in the sample (a rare template), misincorporations can have a great impact on the sequence obtained because fewer sequences are obtained with which to compare to each other or with a reference sequence.

There is, therefore, a need in the art for improved methods for improving the accuracy of nucleic acid synthesis reactions, especially in single molecule sequencing.

SUMMARY OF THE INVENTION

The invention improves the accuracy of nucleic acid sequencing reactions. According to the invention, a template nucleic acid is hybridized to a primer and template-dependent sequencing-by-synthesis is conducted to extend the 3' end of the primer. The template is then removed from the extended primer and the primer is then "primed" and re-sequenced. Practice of the invention allows resequencing of the same sequence and its complement in situ, and results in increased accuracy of sequence determination.

According to the invention, a polymerization reaction is conducted on a nucleic acid duplex that comprises a primer hybridized to a template nucleic acid. The reaction is conducted in the presence of a polymerase, and at least one nucleotide comprising a detectable label. If the nucleotide is complementary to the next nucleotide in the template, it is added to the primer by the polymerase. The added nucleotide is detected and the reaction is then repeated at least once. Thus, the primer is extended by one or more nucleotides corresponding to sequence that is complementary to at least a portion of the template. The template is removed from the duplex, leaving the extended primer.

In one embodiment, one or more primer/template duplexes are bound to a solid support such that a least some of the duplexes are individually optically detectable. The duplexes are exposed to a polymerase, and at least one detectably-labeled nucleotide under conditions sufficient for template-dependent nucleotide addition to the primer. Unincorporated labeled nucleotides are optionally washed away. The incorporation of the labeled nucleotide is detected, thereby identifying the added nucleotide and the complementary template nucleotide. Base addition, washing, and identification steps can be serially repeated in the presence of detectably labeled nucleotide that corresponds to each of the other nucleotide species. As a result, the primer is extended by the added nucleotides. The added nucleotides correspond to sequence that is complementary to at least a portion of the template.

After one or more primer extension steps, the template is removed from the duplex. The template can be removed by any suitable means, for example by raising the temperature of the surface or the flow cell such that the duplex is melted, or by changing the buffer conditions to destabilize the duplex, or combination thereof. Methods for melting template/primer duplexes are well known in the art and are described, for example, in chapter 10 of Molecular Cloning, a Laboratory Manual, $3^{rd}$ Edition, J. Sambrook, and D. W. Russell, Cold Spring Harbor Press (2001), the teachings of which are incorporated herein by reference. The template can then be removed from the surface, for example, by rinsing the surface with a suitable rinsing solution.

After removing the template, the extended primer used in the polymerization reaction remains on the surface. The 3' terminus of the primer is then modified by addition of a short polynucleotide. The polynucleotide is added to the primer by enzymatic catalysis. A preferred enzyme is a ligase or a polymerase. Suitable ligases include, for example, T4 DNA ligase and T4 RNA ligase (such ligases are available commercially, from New England BioLabs (on the World Wide Web at NEB.com) and others capable of adding nucleotides to the 3' terminus of the primer. In a preferred embodiment, a dephosphorylated polynucleotide is added to the primer. Methods for using ligases and dephosphorylating oligonucleotides are well known in the art.

If polymerization is used to add polynucleotides to the 3' terminus of the primer, any suitable enzyme can be used. For example, a polymerase, such as poly(A) polymerase, including yeast poly(A) polymerase, commercially available from USB (on the World Wide Web at USBweb.com), terminal deoxyribonucleotidyl transferase (TdT), and the like are useful. The polymerases can be used according to the manufacturer's instructions.

Having been modified as described above, the primer is then used as a template for template-dependent sequencing-by-synthesis as described generally above.

The polynucleotide added to the primer is chosen such that it is complementary to a new primer (or at least a portion thereof). In a preferred embodiment, the polynucleotide is a homopolymer, such as oligo(dA), and the corresponding primer includes an oligo(dT) sequence. The complementary sequences are of a length suitable for hybridization. The added polynucleotide and its complementary new primer can be about 10 to about 100 nucleotides in length, and preferably about 50 nucleotides in length. The added polynucleotide and new primer can be of the same length or of different lengths. It is routine in the art to adjust primer length and/or oligonucleotide length to optimize hybridization.

Once a polynucleotide is added to the 3' end of the primer and a new primer sequence is hybridized to the polynucleotide (or portion thereof), template-dependent sequencing-by-synthesis is conducted on the primer in the opposite direction of the original sequencing reaction (i.e., toward to surface to which the primer is bound).

After conducting the sequencing reaction back toward to the surface, the "new" extended primer can be melted off, leaving a template having the complementary sequence as the original template for optional resequencing in the 3' to 5' direction (i.e., toward the surface).

Sequencing and/or resequencing at least a portion of the complement of the original template increases the accuracy of the sequence information obtained from a given template by providing more than one set of sequence information to compare, for example, to a reference sequence. In another embodiment, the sequence initially obtained can be compared to the sequence obtained from the new template.

Sequencing methods of the invention preferably comprise template/primer duplex attached to a surface. Individual nucleotides added to the surface comprise a detectable label—preferably an optically-detectable label, such as a fluorescent label. Each nucleotide species can comprise a different label, or can comprise the same label. In a preferred embodiment, each duplex is individually optically resolvable in order to facilitate single molecule sequence discrimination. The choice of a surface for attachment of duplex depends upon the detection method employed. Preferred surfaces for methods of the invention include epoxide surfaces and polyelectrolyte multilayer surfaces, such as those described in Braslavsky, et al., supra. Surfaces preferably are deposited on a substrate that is amenable to optical detection of the surface chemistry, such as glass or silica.

Nucleotides useful in the invention include any nucleotide or nucleotide analog, whether naturally-occurring or synthetic. For example, preferred nucleotides include phosphate esters of deoxyadenosine, deoxycytidine, deoxyguanosine, deoxythymidine, adenosine, cytidine, guanosine, and uridine.

Polymerases useful in the invention include any nucleic acid polymerase capable of catalyzing a template-dependent addition of a nucleotide or nucleotide analog to a primer. Depending on the characteristics of the target nucleic acid, a DNA polymerase, an RNA polymerase, a reverse transcriptase, or a mutant or altered form of any of the foregoing can be used. According to one aspect of the invention, a thermophilic polymerase is used, such as ThermoSequenase®, 9° N™, Therminator™, Taq, Tne, Tma, Pfu, Tfl, Tth, Tli, Stoffel fragment, Vent™ and Deep Vent™ DNA polymerase.

BRIEF DESCRIPTION OF THE DRAWING

The FIGURE shows a schematic representation of one embodiment of the present invention.

DETAILED DESCRIPTION

The invention provides methods and compositions for improving the accuracy of nucleic acid sequencing-by-synthesis reactions by re-sequencing a least a portion of a template nucleic acid. While applicable to bulk sequencing methods, the invention is particularly useful in connection with single molecule sequencing methods. According to the invention, the methods comprise the steps of exposing a duplex comprising a template and a primer to a polymerase and one or more nucleotide comprising a detectable label under conditions sufficient for template-dependent nucleotide addition to the primer. In one embodiment, the template is individually optically resolvable. Any unincorporated labeled nucleotide is optionally washed way. Any nucleotide incorporated into the primer is identified by detecting the label associated with the incorporated nucleotide. The steps of exposing duplex to polymerase and another nucleotide comprising a detectable label and polymerizing, optional washing, and identification are repeated, thereby determining a nucleotide sequence. As a result of the exposing and polymerizing steps, the primer is extended by the addition of one or more nucleotides that are complementary to the corresponding positions of the template. The template is then removed from the duplex, leaving the extended primer. A polynucleotide is added to the 3' terminus of the primer or extended primer, thereby forming a modified primer. The modified primer is used as the template in subsequent sequencing reactions.

The FIGURE is a schematic representation of one embodiment of the invention. In this embodiment, a primer, 2, is attached to a solid support, 3. A template, 1, is hybridized to the primer, forming a template/primer duplex. In step A, the template primer/duplex is exposed to a polymerase and at least one nucleotide comprising a detectable label, under conditions sufficient for template-dependent nucleotide addition to said primer. If the nucleotide is complementary to the template nucleotide immediately downstream of the primer, a nucleotide is added to the primer. After identifying nucleotide incorporated into the primer, the process is repeated, thereby adding a second nucleotide to the primer in a template dependent manner, and so on. As shown in the FIGURE, as a result of repeating the process, template complementary sequence, 4, is added to the primer. After the process has been repeated the desired number of times, the template is removed as shown in step B, leaving the extended primer. In step C, a polynucleotide, 6, is added to the extended primer at the 3' terminus (e.g., downstream of the previously added template complementary sequence) forming a new template for sequencing in the opposite direction. In step D, a primer capable of hybridizing to the polynucleotide is added, forming a template/primer duplex, 7. The process of adding nucleotide and polymerase, detecting incorporated nucleotide and repeating the desired number of times is then repeated using the modified extended primer as a template, as shown in step E, thereby sequencing the template complementary sequence 4, 8. As a result, the primer, 6, is extended by the addition of sequence 8 that corresponds to at least a portion of the original template, 1. The extended primer (6, 8) can be removed, F, and the template can be resequenced, as described above.

In a preferred embodiment of the invention, direct amine attachment is used to attach primer or template to an epoxide surface. The primer or the template can comprise an optically-detectable label in order to determine the location of duplex on the surface. At least a portion of the duplex is optically resolvable from other duplexes on the surface. The surface is preferably passivated with a reagent that occupies portions of the surface that might, absent passivation, fluoresce. Optimal passivation reagents include amines, phosphate, water, sulfates, detergents, and other reagents that reduce native or accumulating surface fluorescence. Sequencing is then accomplished by presenting one or more labeled nucleotide in the presence of a polymerase under conditions that promote complementary base incorporation in the primer. In a preferred embodiment, one base at a time (per cycle) is added and all bases have the same label. There is a wash step after each incorporation cycle, and the label is either neutralized without removal or removed from incorporated nucleotides. After the completion of a predetermined number of cycles of base addition, the linear sequence data for each individual duplex is compiled. Numerous algorithms are available for sequence compilation and alignment as discussed below.

In general, epoxide-coated glass surfaces are used for direct amine attachment of templates, primers, or both. Amine attachment to the termini of template and primer molecules is accomplished using terminal transferase. Primer molecules can be custom-synthesized to hybridize to templates for duplex formation.

A full-cycle is conducted as many times as necessary to complete sequencing of a desired length of template, or resequencing of the desired length of the template complementary sequence. Once the desired number of cycles is complete, the result is a stack of images represented in a computer database. For each spot on the surface that contained an initial individual duplex, there will be a series of light and dark image coordinates, corresponding to whether a base was incorporated in any given cycle. For example, if the template sequence was TACGTACG and nucleotides were presented in the order CAGU(T), then the duplex would be "dark" (i.e., no detectable signal) for the first cycle (presentation of C), but would show signal in the second cycle (presentation of A, which is complementary to the first T in the template sequence). The same duplex would produce signal upon presentation of the G, as that nucleotide is complementary to the next available base in the template, C. Upon the next cycle (presentation of U), the duplex would be dark, as the next base in the template is G. Upon presentation of numerous cycles, the sequence of the template would be built up through the image stack. The sequencing data are then fed into an aligner as described below for resequencing, or are compiled for de novo sequencing as the linear order of nucleotides incorporated into the primer.

The imaging system used in practice of the invention can be any system that provides sufficient illumination of the sequencing surface at a magnification such that single fluorescent molecules can be resolved.

General Considerations

A. Nucleic Acid Templates

Nucleic acid templates include deoxyribonucleic acid (DNA) and/or ribonucleic acid (RNA). Nucleic acid template molecules can be isolated from a biological sample containing a variety of other components, such as proteins, lipids and non-template nucleic acids. Nucleic acid template molecules can be obtained from any cellular material, obtained from an animal, plant, bacterium, fungus, or any other cellular organism. Biological samples for use in the invention also include viral particles or samples prepared from viral material. Nucleic acid template molecules may be obtained directly from an organism or from a biological sample obtained from an organism, e.g., from blood, urine, cerebrospinal fluid, seminal fluid, saliva, sputum, stool and tissue. Any tissue or body fluid specimen may be used as a source for nucleic acid for use in the invention. Nucleic acid template molecules may also be isolated from cultured cells, such as a primary cell culture or a cell line. The cells or tissues from which template nucleic acids are obtained can be infected with a virus or other intracellular pathogen. A sample can also be total RNA extracted from a biological specimen, a cDNA library, viral, or genomic DNA.

Nucleic acid obtained from biological samples typically is fragmented to produce suitable fragments for analysis. In one embodiment, nucleic acid from a biological sample is fragmented by sonication. Nucleic acid template molecules can be obtained as described in U.S. patent application 2002/0190663 A1, published Oct. 9, 2003, the teachings of which are incorporated herein in their entirety. Generally, nucleic acid can be extracted from a biological sample by a variety of techniques such as those described by Maniatis, et al., Molecular Cloning: A Laboratory Manual, Cold Spring Harbor, N.Y., pp. 280-281 (1982). Generally, individual nucleic acid template molecules can be from about 5 bases to about 20 kb. Nucleic acid molecules may be single-stranded, double-stranded, or double-stranded with single-stranded regions (for example, stem- and loop-structures).

A biological sample as described herein may be homogenized or fractionated in the presence of a detergent or surfactant. The concentration of the detergent in the buffer may be about 0.05% to about 10.0%. The concentration of the detergent can be up to an amount where the detergent remains soluble in the solution. In a preferred embodiment, the concentration of the detergent is between 0.1% to about 2%. The detergent, particularly a mild one that is nondenaturing, can act to solubilize the sample. Detergents may be ionic or nonionic. Examples of nonionic detergents include triton, such as the Triton® X series (Triton® X-100 t-Oct-$C_6H_4$—(OCH$_2$—CH$_2$)$_x$OH, x=9-10, Triton® X-100R, Triton® X-114 x=7-8), octyl glucoside, polyoxyethylene(9) dodecyl ether, digitonin, IGEPAL® CA630 octylphenyl polyethylene glycol, n-octyl-beta-D-glucopyranoside (betaOG), n-dodecyl-beta, Tween® 20 polyethylene glycol sorbitan monolaurate, Tween® 80 polyethylene glycol sorbitan monooleate, polidocanol, n-dodecyl beta-D-maltoside (DDM), NP-40 nonylphenyl polyethylene glycol, C12E8 (octaethylene glycol n-dodecyl monoether), hexaethyleneglycol mono-n-tetradecyl ether (C14EO6), octyl-beta-thio-glucopyranoside (octyl thioglucoside, OTG), Emulgen, and polyoxyethylene 10 lauryl ether (C12E10). Examples of ionic detergents (anionic or cationic) include deoxycholate, sodium dodecyl sulfate (SDS), N-lauroylsarcosine, and cetyltrimethylammoniumbromide (CTAB). A zwitterionic reagent may also be used in the purification schemes of the present invention, such as Chaps, zwitterion 3-14, and 3-[(3-cholamidopropyl)dimethylammonio]-1-propanesulfonate. It is contemplated also that urea may be added with or without another detergent or surfactant.

Lysis or homogenization solutions may further contain other agents, such as reducing agents. Examples of such reducing agents include dithiothreitol (DTT), β-mercaptoethanol, DTE, GSH, cysteine, cysteamine, tricarboxyethyl phosphine (TCEP), or salts of sulfurous acid.

B. Nucleotides

Nucleotides useful in the invention include any nucleotide or nucleotide analog, whether naturally-occurring or synthetic. For example, preferred nucleotides include phosphate esters of deoxyadenosine, deoxycytidine, deoxyguanosine, deoxythymidine, adenosine, cytidine, guanosine, and uridine. Other nucleotides useful in the invention comprise an adenine, cytosine, guanine, thymine base, a xanthine or hypoxanthine; 5-bromouracil, 2-aminopurine, deoxyinosine, or methylated cytosine, such as 5-methylcytosine, and N4-methoxydeoxycytosine. Also included are bases of polynucleotide mimetics, such as methylated nucleic acids, e.g., 2'-O-methRNA, peptide nucleic acids, modified peptide nucleic acids, locked nucleic acids and any other structural moiety that can act substantially like a nucleotide or base, for example, by exhibiting base-complementarity with one or more bases that occur in DNA or RNA and/or being capable of base-complementary incorporation, and includes chain-terminating analogs. A nucleotide corresponds to a specific nucleotide species if they share base-complementarity with respect to at least one base.

Nucleotides for nucleic acid sequencing according to the invention preferably comprise a detectable label that is directly or indirectly detectable. Preferred labels include optically-detectable labels, such as fluorescent labels. Examples of fluorescent labels include, but are not limited to, 4-acetamido-4'-isothiocyanatostilbene-2,2'disulfonic acid; acridine and derivatives: acridine, acridine isothiocyanate; 5-(2'-aminoethyl)aminonaphthalene-1-sulfonic acid (EDANS); 4-amino-N-[3-vinylsulfonyl)phenyl]naphthalimide-3,5 disulfonate; N-(4-anilino-1-naphthyl)maleimide; anthranilamide; BODIPY; Brilliant Yellow; coumarin and derivatives; coumarin, 7-amino-4-methylcoumarin (AMC, Coumarin 120), 7-amino-4-trifluoromethylcouluarin (Coumaran 151); cyanine dyes; cyanosine; 4',6-diaminidino-2-phenylindole (DAPI); 5'5"-dibromopyrogallol-sulfonaphthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansylchloride); 4-dimethylaminophenylazophenyl-4'-isothiocyanate (DABITC); eosin and derivatives; eosin, eosin isothiocyanate, erythrosin and derivatives; erythrosin B, erythrosin, isothiocyanate; ethidium; fluorescein and derivatives; 5-carboxyfluorescein (FAM), 5-(4,6-dichlorotriazin-2-yl)aminofluorescein (DTAF), 2',7'-dimethoxy-4'5'-dichloro-6-carboxyfluorescein, fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin; o-phthaldialdehyde; pyrene and derivatives: pyrene, pyrene butyrate, succinimidyl 1-pyrene; butyrate quantum dots; Reactive Red 4 (Cibacron™ Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red); N,N,N',N'tetramethyl-6-carboxyrhodamine (TAMRA); tetramethyl rhodamine; tetramethyl rhodamine isothiocyanate (TRITC); riboflavin; rosolic acid; terbium chelate derivatives; Cy3; Cy5; Cy5.5; Cy7; IRD 700; IRD 800; La Jolta Blue; phthalo cyanine; and naphthalo cyanine. Preferred fluorescent labels are cyanine-3 and cyanine-5. Labels other than fluorescent labels are contemplated by the invention, including other optically-detectable labels.

C. Nucleic Acid Polymerases

Nucleic acid polymerases generally useful in the invention include DNA polymerases, RNA polymerases, reverse transcriptases, and mutant or altered forms of any of the foregoing. DNA polymerases and their properties are described in detail in, among other places, DNA Replication 2nd edition, Kornberg and Baker, W. H. Freeman, New York, N.Y. (1991). Known conventional DNA polymerases useful in the invention include, but are not limited to, *Pyrococcus furiosus* (Pfu) DNA polymerase (Lundberg et al., 1991, Gene, 108: 1, Stratagene), *Pyrococcus woesei* (Pwo) DNA polymerase (Hinnisdaels et al., 1996, Biotechniques, 20:186-8, Boehringer Mannheim), *Thermus thermophilus* (Tth) DNA polymerase (Myers and Gelfand 1991, Biochemistry 30:7661), *Bacillus stearothermophilus* DNA polymerase (Stenesh and McGowan, 1977, Biochim Biophys Acta 475:32), *Thermococcus litoralis* (Tli) DNA polymerase (also referred to as Vent™ DNA polymerase, Cariello et al., 1991, Polynucleotides Res, 19: 4193, New England Biolabs), 9° Nm™ DNA polymerase (New England Biolabs), Stoffel fragment, ThermoSequenase® (Amersham Pharmacia Biotech UK), Terminator™ (New England Biolabs), *Thermotoga maritima* (Tma) DNA polymerase (Diaz and Sabino, 1998 Braz J Med. Res, 31:1239), *Thermus aquaticus* (Taq) DNA polymerase (Chien et al., 1976, J. Bacteriol, 127: 1550), DNA polymerase, *Pyrococcus kodakaraensis* KOD DNA polymerase (Takagi et al., 1997, Appl. Environ. Microbiol. 63:4504), JDF-3 DNA polymerase (from *thermococcus* sp. JDF-3, Patent application WO 0132887), *Pyrococcus* GB-D (PGB-D) DNA polymerase (also referred as Deep Vent™ DNA polymerase, Juncosa-Ginesta et al., 1994, Biotechniques, 16:820, New England Biolabs), UlTma DNA polymerase (from thermophile *Thermotoga maritima*; Diaz and Sabino, 1998 Braz J. Med. Res, 31:1239; PE Applied Biosystems), Tgo DNA polymerase (from *thermococcus gorgonarius*, Roche Molecular Biochemicals), *E. coli* DNA polymerase I (Lecomte and Doubleday, 1983, Polynucleotides Res. 11:7505), T7 DNA polymerase (Nordstrom et al., 1981, J Biol. Chem. 256:3112), and archaeal DP1I/DP2 DNA polymerase II (Cann et al., 1998, Proc Natl Acad. Sci. USA 95:14250-->5).

While mesophilic polymerases are contemplated by the invention, preferred polymerases are thermophilic. Thermophilic DNA polymerases include, but are not limited to, ThermoSequenase®, 9° Nm™, Terminator™, Taq, Tne, Tma, Pfu, Tfl, Tth, Tli, Stoffel fragment, Vent™ and Deep Vent™ DNA polymerase, KOD DNA polymerase, Tgo, JDF-3, and mutants, variants and derivatives thereof.

Reverse transcriptases useful in the invention include, but are not limited to, reverse transcriptases from HIV, HTLV-1, HTLV-II, FeLV, FIV, SIV, AMV, MMTV, MoMuLV and other retroviruses (see Levin, *Cell* 88:5-8 (1997); Verma, Biochim Biophys Acta. 473:1-38 (1977); Wu et al., CRC Crit Rev Biochem. 3:289-347 (1975)).

D. Surfaces

In a preferred embodiment, nucleic acid template molecules are attached to a substrate (also referred to herein as a surface) and subjected to analysis by sequencing as taught herein. Nucleic acid template molecules are attached to the surface such that the template/primer duplexes are individually optically resolvable. Substrates for use in the invention can be two- or three-dimensional and can comprise a planar surface (e.g., a glass slide) or can be shaped. A substrate can include glass (e.g., controlled pore glass (CPG)), quartz, plastic (such as polystyrene (low cross-linked and high cross-linked polystyrene), polycarbonate, polypropylene and poly(methymethacrylate)), acrylic copolymer, polyamide, silicon, metal (e.g., alkanethiolate-derivatized gold), cellulose, nylon, latex, dextran, gel matrix (e.g., silica gel), polyacrolein, or composites.

Suitable three-dimensional substrates include, for example, spheres, microparticles, beads, membranes, slides, plates, micromachined chips, tubes (e.g., capillary tubes), microwells, microfluidic devices, channels, filters, or any other structure suitable for anchoring a nucleic acid. Substrates can include planar arrays or matrices capable of having regions that include populations of template nucleic acids or primers. Examples include nucleoside-derivatized CPG and polystyrene slides; derivatized magnetic slides; polystyrene grafted with polyethylene glycol, and the like.

In one embodiment, a substrate is coated to allow optimum optical processing and nucleic acid attachment. Substrates for use in the invention can also be treated to reduce background. Exemplary coatings include epoxides, and derivatized epoxides (e.g., with a binding molecule, such as streptavidin). The surface can also be treated to improve the positioning of attached nucleic acids (e.g., nucleic acid template molecules, primers, or template molecule/primer duplexes) for analysis. As such, a surface according to the invention can be treated with one or more charge layers (e.g., a negative charge) to repel a charged molecule (e.g., a negatively charged labeled nucleotide). For example, a substrate according to the invention can be treated with polyallylamine followed by polyacrylic acid to form a polyelectrolyte multilayer. The carboxyl groups of the polyacrylic acid layer are negatively charged and thus repel negatively charged labeled nucleotides, improving the positioning of the label for detection. Coatings or films applied to the substrate should be able to withstand subsequent treatment steps (e.g., photoexposure, boiling, baking, soaking in warm detergent-containing liquids, and the like) without substantial degradation or disassociation from the substrate.

Examples of substrate coatings include, vapor phase coatings of 3-aminopropyltrimethoxysilane, as applied to glass slide products, for example, from Molecular Dynamics, Sunnyvale, Calif. In addition, generally, hydrophobic substrate coatings and films aid in the uniform distribution of hydrophilic molecules on the substrate surfaces. Importantly, in those embodiments of the invention that employ substrate coatings or films, the coatings or films that are substantially non-interfering with primer extension and detection steps are preferred. Additionally, it is preferable that any coatings or films applied to the substrates either increase template molecule binding to the substrate or, at least, do not substantially impair template binding.

Various methods can be used to anchor or immobilize the primer to the surface of the substrate. The immobilization can be achieved through direct or indirect bonding to the surface. The bonding can be by covalent linkage. See, Joos et al., Analytical Biochemistry 247:96-101, 1997; Oroskar et al., Clin. Chem. 42:1547-1555, 1996; and Khandjian, Mol. Bio. Rep. 11:107-115, 1986. A preferred attachment is direct amine bonding of a terminal nucleotide of the template or the primer to an epoxide integrated on the surface. The bonding also can be through non-covalent linkage. For example, biotin-streptavidin (Taylor et al., J. Phys. D. Appl. Phys. 24:1443, 1991) and digoxigenin with anti-digoxigenin (Smith et al., Science 253:1122, 1992) are common tools for anchoring nucleic acids to surfaces and parallels. Alternatively, the attachment can be achieved by anchoring a hydrophobic chain into a lipid monolayer or bilayer. Other methods for known in the art for attaching nucleic acid molecules to substrates also can be used.

E. Detection

Any detection method may be used that is suitable for the type of label employed. Thus, exemplary detection methods include radioactive detection, optical absorbance detection, e.g., UV-visible absorbance detection, optical emission detection, e.g., fluorescence or chemiluminescence. For example, extended primers can be detected on a substrate by scanning all or portions of each substrate simultaneously or serially, depending on the scanning method used. For fluorescence labeling, selected regions on a substrate may be serially scanned one-by-one or row-by-row using a fluorescence microscope apparatus, such as described in Fodor (U.S. Pat. No. 5,445,934) and Mathies et al. (U.S. Pat. No. 5,091,652). Devices capable of sensing fluorescence from a single molecule include scanning tunneling microscope (siM) and the atomic force microscope (AFM). Hybridization patterns may also be scanned using a CCD camera (e.g., Model TE/CCD512SF, Princeton Instruments, Trenton, N.J.) with suitable optics (Ploem, in Fluorescent and Luminescent Probes for Biological Activity Mason, T. G. Ed., Academic Press, Landon, pp. 1-11 (1993), such as described in Yershov et al., Proc. Natl. Aca. Sci. 93:4913 (1996), or may be imaged by TV monitoring. For radioactive signals, a phosphorimager device can be used (Johnston et al., Electrophoresis, 13:566, 1990; Drmanac et al., Electrophoresis, 13:566, 1992; 1993). Other commercial suppliers of imaging instruments include General Scanning Inc., (Watertown, Mass. on the World Wide Web at genscan.com), Genix Technologies (Waterloo, Ontario, Canada; on the World Wide Web at confocal.com), and Applied Precision Inc. Such detection methods are particularly useful to achieve simultaneous scanning of multiple attached template nucleic acids.

A number of approaches can be used to detect incorporation of fluorescently-labeled nucleotides into a single nucleic acid molecule. Optical setups include near-field scanning microscopy, far-field confocal microscopy, widefield epi-illumination, light scattering, dark field microscopy, photoconversion, single and/or multiphoton excitation, spectral wavelength discrimination, fluorophore identification, evanescent wave illumination, and total internal reflection fluorescence (TIRF) microscopy. In general, certain methods involve detection of laser-activated fluorescence using a microscope equipped with a camera. Suitable photon detection systems include, but are not limited to, photodiodes and intensified CCD cameras. For example, an intensified charge couple device (ICCD) camera can be used. The use of an ICCD camera to image individual fluorescent dye molecules in a fluid near a surface provides numerous advantages. For example, with an ICCD optical setup, it is possible to acquire a sequence of images (movies) of fluorophores.

Some embodiments of the present invention use TIRF microscopy for two-dimensional imaging. TIRF microscopy uses totally internally reflected excitation light and is well known in the art. See, e.g., the World Wide Web at nikon-instruments.jp/eng/page/products/tirf.aspx. In certain embodiments, detection is carried out using evanescent wave illumination and total internal reflection fluorescence microscopy. An evanescent light field can be set up at the surface, for example, to image fluorescently-labeled nucleic acid molecules. When a laser beam is totally reflected at the interface between a liquid and a solid substrate (e.g., a glass), the excitation light beam penetrates only a short distance into the liquid. The optical field does not end abruptly at the reflective interface, but its intensity falls off exponentially with distance. This surface electromagnetic field, called the "evanescent wave", can selectively excite fluorescent molecules in the liquid near the interface. The thin evanescent optical field at the interface provides low background and facilitates the detection of single molecules with high signal-to-noise ratio at visible wavelengths.

The evanescent field also can image fluorescently-labeled nucleotides upon their incorporation into the attached template/primer complex in the presence of a polymerase. Total internal reflectance fluorescence microscopy is then used to visualize the attached template/primer duplex and/or the incorporated nucleotides with single molecule resolution.

F. Analysis

Alignment and/or compilation of sequence results obtained from the image stacks produced as generally described above utilizes look-up tables that take into account possible sequences changes (due, e.g., to errors, mutations, etc.). Essentially, sequencing results obtained as described herein are compared to a look-up type table that contains all possible reference sequences plus 1 or 2 base errors.

In resequencing, a preferred embodiment for sequence alignment compares sequences obtained to a database of reference sequences of the same length, or within 1 or 2 bases of the same length, from the initially obtained sequence or the target sequence contained in a look-up table format. In a preferred embodiment, the look-up table contains exact matches with respect to the reference sequence and sequences of the prescribed length or lengths that have one or two errors (e.g., 9-mers with all possible 1-base or 2-base errors). The obtained sequences are then matched to the sequences on the look-up table and given a score that reflects the uniqueness of the match to sequence(s) in the table. The obtained sequences are then aligned to the reference sequence based upon the position at which the obtained sequence best matches a portion of the reference sequence. More detail on the alignment process is provided below in the Example.

EXAMPLE

The 7249 nucleotide genome of the bacteriophage M13mp18 was sequenced using single molecule methods of the invention. Purified, single-stranded viral M13mp18 genomic DNA was obtained from New England Biolabs. Approximately 25 ug of M13 DNA was digested to an average fragment size of 40 bp with 0.1 U Dnase I (New England Biolabs) for 10 minutes at 37° C. Digested DNA fragment sizes were estimated by running an aliquot of the digestion mixture on a precast denaturing (TBE-Urea) 10% polyacrylamide gel (Novagen) and staining with SYBR Gold (Invitrogen/Molecular Probes). The DNase I-digested genomic DNA was filtered through a YM10 ultrafiltration spin column (Millipore) to remove small digestion products less than about 30 nt. Approximately 20 pmol of the filtered DNase I digest was then polyadenylated with terminal transferase according to known methods (Roychoudhury, R and Wu, R. 1980, Terminal transferase-catalyzed addition of nucleotides to the 3' termini of DNA. Methods Enzymol. 65(1):43-62.). The average dA tail length was 50+/−5 nucleotides. Terminal transferase was then used to label the fragments with Cy3-dUTP. Fragments were then terminated with dideoxyTTP (also added using terminal transferase). The resulting fragments were again filtered with a YM10 ultrafiltration spin column to remove free nucleotides and stored in ddH$_2$O at −20° C.

Epoxide-coated glass slides were prepared for oligo attachment. Epoxide-functionalized 40 mm diameter #1.5 glass cover slips (slides) were obtained from Erie Scientific (Salem, N.H.). The slides were preconditioned by soaking in 3×SSC for 15 minutes at 37° C. Next, a 500 µM aliquot of 5' aminated polydT(50) primer (polythymidine of 50 nucleotides in length with a 5' terminal amine) is incubated with each slide for 30 minutes at room temperature in a volume of 80 ml. The resulting slides have primer attached by direct amine linkage to the epoxide. The slides are then treated with phosphate (1 M) for 4 hours at room temperature in order to passivate the surface. Slides re then stored in polymerase rinse buffer (20 mM Tris, 100 mM NaCl, 0.001% Triton X-100, pH 8.0) until they are used for sequencing.

For sequencing, the slides are placed in a modified FCS2 flow cell (Bioptechs, Butler, Pa.) using a 50 um thick gasket The flow cell is placed on a movable stage that is part of a high-efficiency fluorescence imaging system built around a Nikon TE-2000 inverted microscope equipped with a total internal reflection (TIR) objective. The slide is then rinsed with HEPES buffer with 100 mM NaCl and equilibrated to a temperature of 50° C. An aliquot of poly(dT50) template is placed in the flow cell and incubated on the slide for 15 minutes. After incubation, the flow cell is rinsed with 1×SSC/HEPES/0.1% SDS followed by HEPES/NaCl. A passive vacuum apparatus is used to pull fluid across the flow cell. The resulting slide contains M13 template/primer duplex. The temperature of the flow cell is then reduced to 37° C. for sequencing and the objective is brought into contact with the flow cell.

For sequencing, cytosine triphosphate, guanidine triphosphate, adenine triphosphate, and uracil triphosphate, each having a cyanine-5 label (at the 7-deaza position for ATP and GTP and at the C5 position for CTP and UTP (PerkinElmer)) are stored separately in buffer containing 20 mM Tris-HCl, pH 8.8, 10 mM MgSO$_4$, 10 mM (NH$_4$)$_2$SO$_4$, 10 mM HCl, and 0.1% Triton X-100, and 100U Klenow exo$^-$ polymerase (NEN). Sequencing proceeds as follows.

First, initial imaging is used to determine the positions of duplex on the epoxide surface. The Cy3 label attached to the M13 templates is imaged by excitation using a laser tuned to 532 nm radiation (Verdi V-2 Laser, Coherent, Inc., Santa Clara, Calif.) in order to establish duplex position. For each slide only single fluorescent molecules imaged in this step are counted. Imaging of incorporated nucleotides as described below is accomplished by excitation of a cyanine-5 dye using a 635 nm radiation laser (Coherent). 5 uM Cy5CTP is placed into the flow cell and exposed to the slide for 2 minutes. After incubation, the slide is rinsed in 1×SSC/15 mM HEPES/0.1% SDS/pH 7.0 ("SSC/HEPES/SDS") (15 times in 60 ul volumes each, followed by 150 mM HEPES/150 mM NaCl/pH 7.0 ("HEPES/NaCl") (10 times at 60 ul volumes). An oxygen scavenger containing 30% acetonitrile and scavenger buffer (134 ul HEPES/NaCl, 24 ul 100 mM Trolox in MES, pH6.1, 10 ul DABCO in MES, pH6.1, 8 ul 2M glucose, 20 ul NaI (50 mM stock in water), and 4 ul glucose oxidase) is next added. The slide is then imaged (500 frames) for 0.2 seconds using an Inova301K laser (Coherent) at 647 nm, followed by green imaging with a Verdi V-2 laser (Coherent) at 532 nm for 2 seconds to confirm duplex position. The positions having detectable fluorescence are recorded. After imaging, the flow cell is rinsed 5 times each with SSC/HEPES/SDS (60 ul) and HEPES/NaCl (60 ul). Next, the cyanine-5 label is cleaved off incorporated CTP by introduction into the flow cell of 50 mM TCEP for 5 minutes, after which the flow cell is rinsed 5 times each with SSC/HEPES/SDS (60 ul) and HEPES/NaCl (60 ul). The remaining nucleotide is capped with 50 mM iodoacetamide for 5 minutes followed by rinsing 5 times each with SSC/HEPES/SDS (60 ul) and HEPES/NaCl (60 ul). The scavenger is applied again in the manner described above, and the slide is again imaged to determine the effectiveness of the cleave/cap steps and to identify non-incorporated fluorescent objects.

The procedure described above is then conducted 100 nM Cy5dATP, followed by 100 nM Cy5dGTP, and finally 500 nM Cy5dUTP. The procedure (expose to nucleotide, polymerase, rinse, scavenger, image, rinse, cleave, rinse, cap, rinse, scavenger, final image) is repeated exactly as described for ATP, GTP, and UTP except that Cy5dUTP is incubated for 5 minutes instead of 2 minutes. Uridine is used instead of Thymidine due to the fact that the Cy5 label is incorporated at the position normally occupied by the methyl group in Thymidine triphosphate, thus turning the dTTP into dUTP. In all 64 cycles (C, A, G, U) are conducted as described in this and the preceding paragraph.

Once the desired number of cycles are completed, the image stack data (i.e., the single molecule sequences obtained from the various surface-bound duplex) are aligned to the M13 reference sequence. The image data obtained can be compressed to collapse homopolymeric regions. Thus, the sequence "TCAAAGC" is represented as "TCAGC" in the data tags used for alignment. Similarly, homopolymeric regions in the reference sequence are collapsed for alignment.

The alignment algorithm matches sequences obtained as described above with the actual M13 linear sequence. Placement of obtained sequence on M13 is based upon the best match between the obtained sequence and a portion of M13 of the same length, taking into consideration 0, 1, or 2 possible errors. All obtained 9-mers with 0 errors (meaning that they exactly match a 9-mer in the M13 reference sequence) are first aligned with M13. Then 10-, 11-, and 12-mers with 0 or 1 error are aligned. Finally, all 13-mers or greater with 0, 1, or 2 errors are aligned.

The template fragments are removed by increasing the temperature of the flow cell above the melting temperature of the duplex, thereby releasing the template fragments from the duplexes. The free templates are removed from the flow cell by washing the flow cell, for example the flow cell can be rinsed 5 times each with SSC/HEPES/SDS (60 ul) and HEPES/NaCl (60 ul).

The primers are then modified by adding a polynucleotide sequence to the 3' terminus of the primer. The oligonucleotide-modified primers are then used as the template in subsequent polymerization reactions. Free primer capable of hybridizing to the added oligonucleotide is added to the flow cell and incubated under conditions sufficient to allow hybridization between the added oligonucleotide portion of the template and the free primer. After incubation, the flow cell is rinsed with 1×SSC/HEPES/0.1% SDS followed by HEPES/NaCl. The resulting slide contains template/primer duplexes where the template comprises the original primer having M13 template complementary sequences added thereto and modified with an oligonucleotide. The temperature of the flow cell is then reduced to 37° C. for sequencing and the objective is brought into contact with the flow cell. The procedure (expose to nucleotide, polymerase, rinse, scavenger, image, rinse, cleave, rinse, cap, rinse, scavenger, final image) is repeated as described above.

Once the desired number of cycles is completed, the image stack data (i.e., the single molecule sequences obtained from the various surface-bound duplex) are aligned to the M13 reference sequence and/or are aligned to the sequence initially obtained as described above. The image data obtained can be compressed to collapse homopolymeric regions as described above.

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are therefore intended to be embraced therein.

I claim:

1. A method of increasing accuracy of nucleic acid sequencing, the method comprising the steps of:
    a) exposing a duplex comprising a template and a primer to a polymerase and one or more nucleotide comprising a detectable label under conditions sufficient for template-dependent nucleotide addition to said primer, wherein said template is individually optically resolvable;
    b) identifying nucleotide incorporated into said primer;
    c) neutralizing said detectable label or removing said detectable label from said incorporated nucleotide;
    d) repeating steps a)-c), thereby determining a nucleotide sequence incorporated into said primer of said duplex;
    e) removing the template from the primer of step d);
    f) adding a polynucleotide to a 3' terminus of the primer from step e) to form a template;
    g) exposing the template of step f) to a primer capable of hybridizing to said added polynucleotide to form template/primer duplex, and repeating steps a) through d) to sequence a portion of the template, wherein at least a portion of the sequence obtained is complementary to the nucleotide sequence of d), thereby increasing the accuracy of nucleic acid sequencing.

2. The method of claim 1, wherein the sequence obtained in c) is compared with a complement of the sequence obtained in f).

3. The method of claim 1, further comprising repeating steps (e) through (g).

4. The method of claim 1, wherein said label is an optically-detectable label.

5. The method of claim 4, wherein said optically-detectable label is a fluorescent label.

6. The method of claim 5, wherein said fluorescent label is selected from the group consisting of fluorescein, rhodamine, cyanine, Cy5, Cy3, BODIPY, alexa, and derivatives thereof.

7. The method of claim 1, wherein said duplex is attached to a surface.

8. The method of claim 1, wherein said primer is attached to a surface.

* * * * *